United States Patent [19]
Reich et al.

[11] Patent Number: 5,860,986
[45] Date of Patent: *Jan. 19, 1999

[54] APPARATUS AND METHOD FOR PREPARING AN INTRAOCULAR LENS FOR INSERTION

[75] Inventors: Cary J. Reich, Laguna Hills; Todd A. Mendelson, Anaheim; Bradley S. Stone, Santa Ana; Michael W. Orchowski, Laguna Beach, all of Calif.

[73] Assignee: Chiron Vision Corporation, Claremont, Calif.

[ * ] Notice: The term of this patent shall not extend beyond the expiration date of Pat. No. 5,653,715.

[21] Appl. No.: 851,989

[22] Filed: May 6, 1997

Related U.S. Application Data

[63] Continuation of Ser. No. 28,281, Mar. 9, 1993, Pat. No. 5,653,715.

[51] Int. Cl.⁶ ....................................................... A61F 9/00
[52] U.S. Cl. ................................................................ 606/107
[58] Field of Search ................................ 606/1, 107, 108, 606/151; 623/4, 6; 604/57

[56] References Cited

U.S. PATENT DOCUMENTS

| | | | |
|---|---|---|---|
| 5,123,905 | 6/1992 | Kelman | 606/107 |
| 5,562,676 | 10/1996 | Brady et al. | 606/107 |
| 5,653,715 | 8/1997 | Reich et al. | 606/107 |

*Primary Examiner*—Glenn K. Dawson
*Attorney, Agent, or Firm*—Pravel, Hewitt, Kimball & Krieger; Rita D. Vacca

[57] ABSTRACT

An IOL compression chamber for folding an IOL includes a hollow chamber having a loading area, a staging area and a distal tip. The loading area has a distally extending slot in the wall, which allows for easy removal of a forceps holding the IOL from the chamber following insertion of the IOL into the chamber with the forceps. The staging area holds the IOL in a folded state until the chamber is placed into an IOL insertion instrument having a plunger which forces the IOL distally out of the staging area and into the eye through the distal tip.

4 Claims, 3 Drawing Sheets

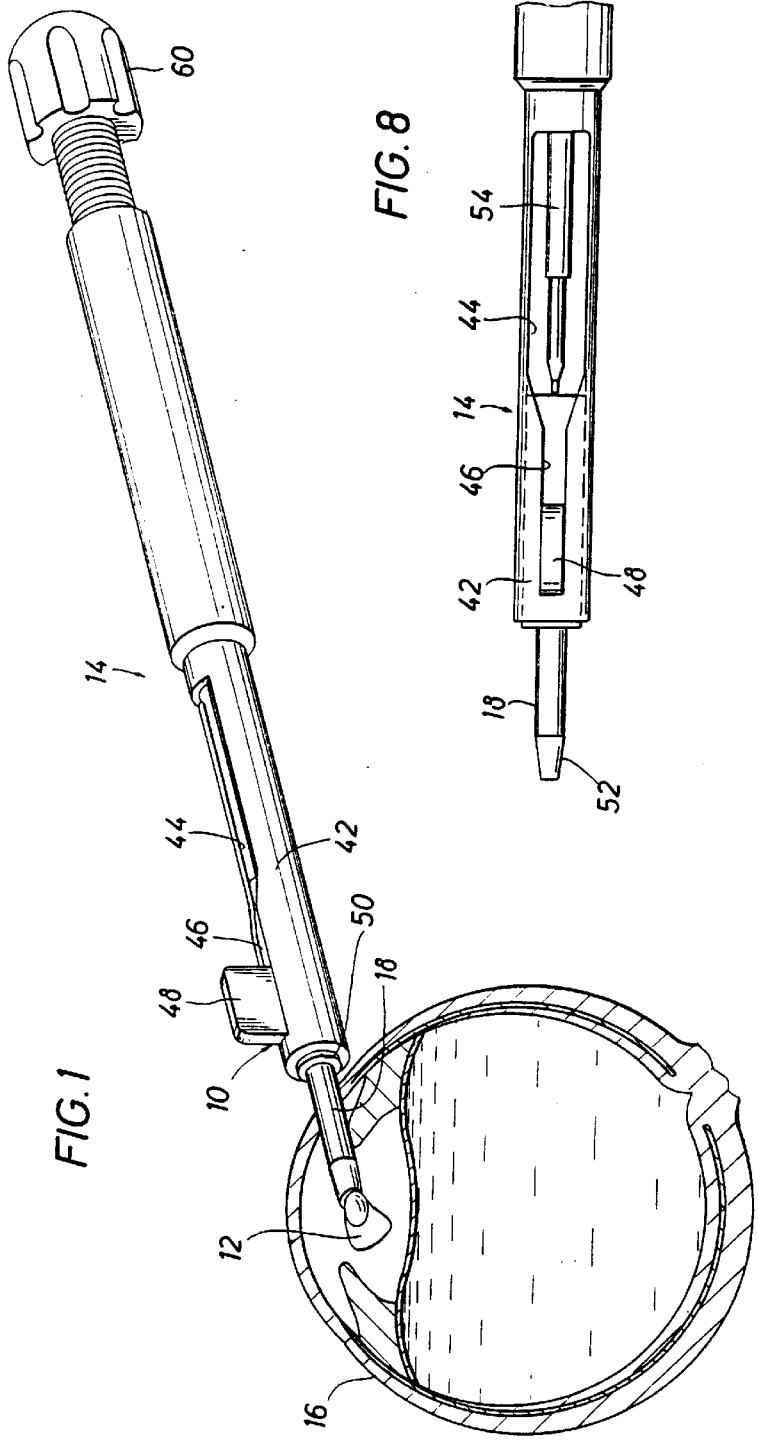
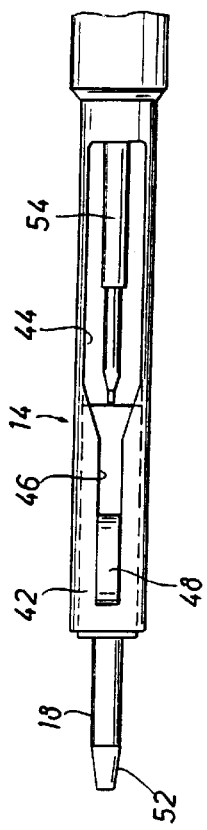
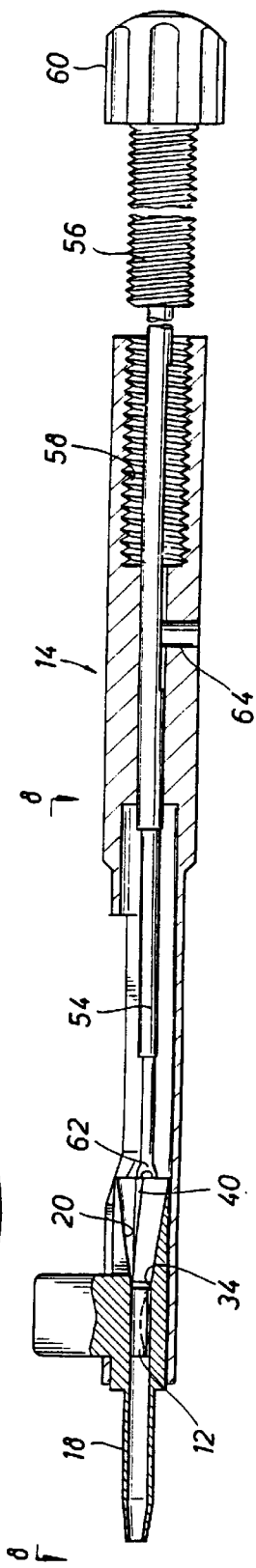

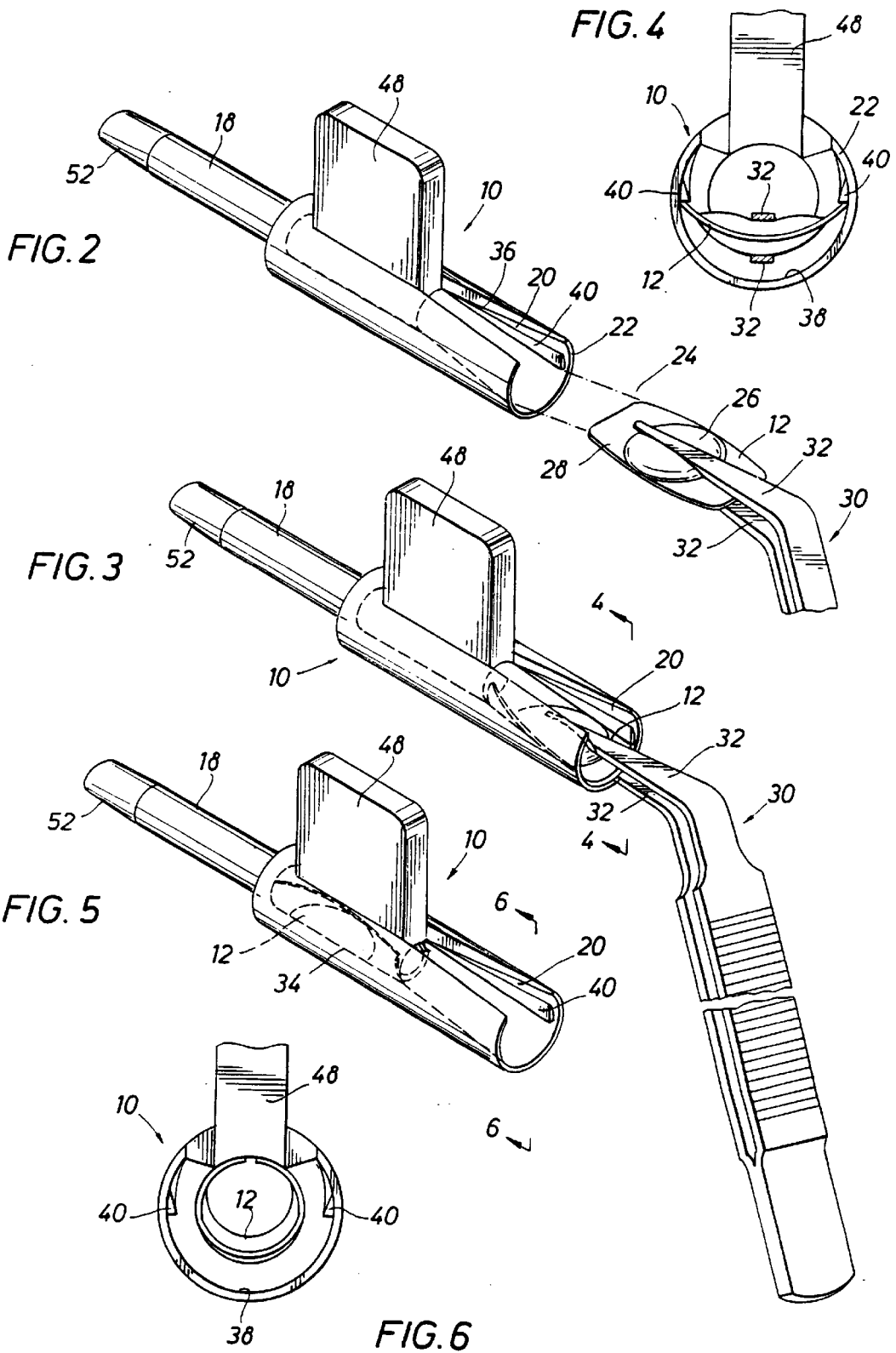

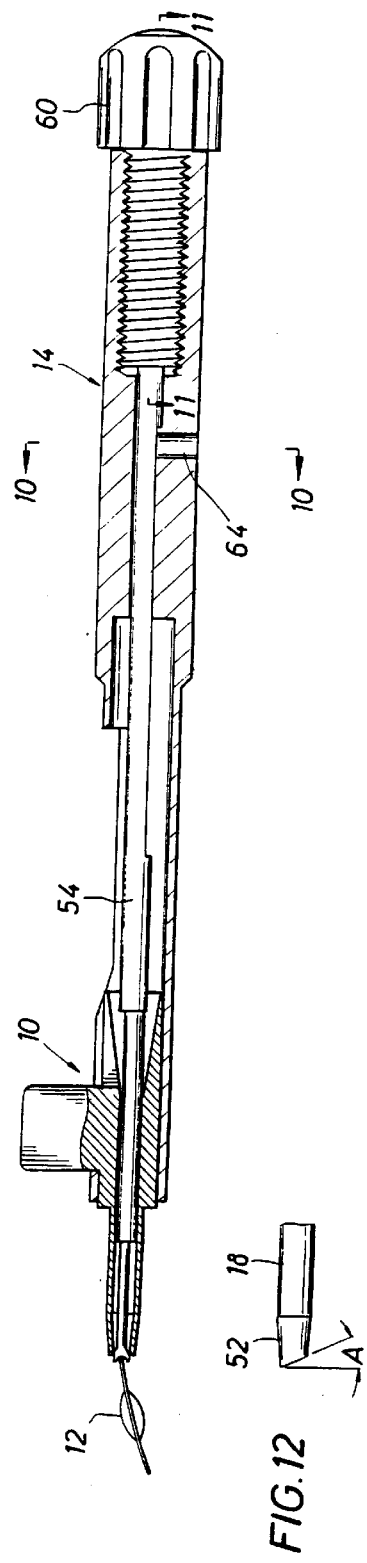
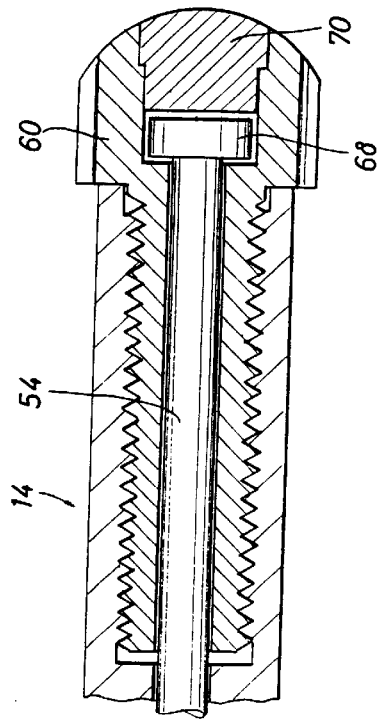
FIG. 9
FIG. 11
FIG. 10
FIG. 12
FIG. 13

APPARATUS AND METHOD FOR PREPARING AN INTRAOCULAR LENS FOR INSERTION

This is a continuation of application Ser. No. 08/028,281 filed Mar. 9, 1993, now U.S. Pat. No. 5,653,715.

BACKGROUND OF THE INVENTION

The present invention relates to intraocular lenses (IOLs) formed of a material such as silicone or a hydrogel that allows the lens to be folded, rolled or otherwise deformed or compressed and, more particularly, an improved apparatus and method for deforming or compressing IOLs of that type and positioning them for insertion into the eye of a patient.

IOLs were developed a number of years ago to replace a clouded natural lens, called a cataract. Cataracts cause individuals to lose their sight, either partially or completely, because clouding prevents light and an image from being transmitted through the lens onto the retina. When the clouding becomes severe, an individual can no longer see. Replacement of the natural lens with an IOL has become an accepted procedure for alleviating the symptoms of a cataract.

Various surgical procedures have been developed for removing a cataract, ranging from physically lifting the lens from the membrane that encapsulates the lens to emulsifying the lens through the use of sound waves and suction equipment. It has been found that this latter procedure, known as phacoemulsification, is advantageous because a much smaller incision is required in the eye, 3 mm or smaller, than other techniques where the lens is removed in tact. A smaller incision is desirable because if sutures are used to close it, the eyeball is deformed less than for larger incisions which are typically up to 6.5–8 mm. Further, with incisions under 3 mm, sutures are generally not required and the incision heals itself. The lack of sutures offers an even further assurance that the ocular globe or eyeball will not be deformed.

A number of different attempts have been made to develop IOLs which can be inserted through the smaller incision openings. Before the availability of IOLs formed of a soft material that could be deformed or compressed, various techniques were attempted to develop a small profile IOL, ranging from forming lenses with a narrower lateral dimension to various types of lenses that could be dismantled or manipulated and rebuilt in the eye.

After IOLs formed of silicon or a hydrogel material became available, IOLs could be folded, rolled or otherwise deformed or compressed so that they could be inserted into the eye through a much smaller incision than previously possible. Such lenses are described and shown, for example, in U.S. Pat. No. 4,573,998 to Mazzocco.

Various techniques and equipment have been developed for folding soft IOLs and inserting them into the eye. These include the use of forceps with relatively long blades which can engage an IOL and hold it in a folded position while it is inserted into the eye as shown, for example, in U.S. Pat. Nos. 5,007,913; 5,100,410 and 5,178,622. The disadvantage of these forceps devices is that they are difficult to operate. As the forcep blades release the IOL, its positioning is not tightly controlled within the eye and movement of the forcep blades could cause the incision to be enlarged. In addition, any movement close to the inner surface of the cornea is undesirable because the forcep blades or lens could rub against the endothelial cells on the inner surface of the cornea, which are not regenerative, and cause permanent damage. Since the forceps are manually squeezed by the surgeon, there is also the possibility that too much pressure could damage various portions of the IOL.

Another type of insertion instrument which has been developed includes a chamber in which an IOL is inserted. The IOL is folded, rolled or otherwise deformed or compressed during the insertion process. The IOL is then pushed or expressed out of an elongated tip by a plunger after the tip is inserted into the eye.

While this type of inserter has the advantage of an elongated tip, which does not have to be opened or closed, projecting through a small incision for precise placement of an IOL, known designs have various moveable parts that are complicated to fabricate and assemble or the folding process requires several steps which prolong and complicate the surgical procedure.

For example, a number of inserters have been developed where an envelope or paddle is moved to project from the distal tip of the inserter, which operates to fold the IOL as it is pulled back into the inserter. The IOL is implanted when the paddle is afterward moved to project from the tip by a physician. See, for example, U.S. Pat. Nos. 4,836,201; 4,880,000; 4,934,363 and 5,098,439. Others have jaw-like portions that operate to fold the IOL as they close or telescopic sections that move relative to each other to hold the lens after it has been folded. See, for example, U.S. Pat. Nos. 4,714,373; 4,747,404 and 4,834,094.

An inserter was also developed, as shown in U.S. Pat. No. 4,919,130, where a cannula is designed to receive an IOL that is partially folded. A first plunger pushes the IOL through a rigid chamber of gradually diminishing diameter to fold it completely. A second plunger then pushes the IOL out of the cannula and into the eye.

In another inserter, shown in U.S. Pat. No. 4,681,102, an IOL is placed in an open cartridge which has two tabs or wing-like sections that are hinged together. The IOL is folded as the sections are closed. The cartridge is then placed in an inserter where an insertion cone, with an opening coextensive with the opening in the cartridge, is either placed over or formed adjacent to the cartridge. A single plunger is used to push the folded lens through the insertion cone and into the eye.

Because of the moving parts in many of the folding devices discussed above, the IOL can easily be pinched or torn during the folding or insertion process. In addition, folding and loading require a certain amount of manual manipulation of the IOL, which takes time and complicates the procedure. In the device where a cannula is used, a first plunger is used to fold the lens, which must be removed and replaced by a second plunger for inserting the lens in the eye.

Thus, there is a perceived need for an apparatus and method for folding an IOL and positioning it for insertion in the eye, which are less complicated than known devices and methods and eliminate moving parts which can pinch and tear the IOL and unneeded steps in the folding process.

SUMMARY OF THE INVENTION

An improved intraocular lens compression chamber and associated insertion instrument and method have been developed which solve the problems discussed above.

The compression chamber has an elongated IOL loading area which has an opening at a proximal lens receiving end that leads to an elongated passageway. The opening is large enough to receive a deformable or compressible IOL held by the blades of a pair of forceps, where the IOL is substantially in its open position. The passageway gradually decreases in size for a predetermined distance so that when the lens is pushed through the passageway, the lens is deformed or compressed by the walls defining the passageway. The lens is engaged and pushed through the passageway by the pair of forceps which can easily be withdrawn after the IOL has been deformed or compressed and placed in a staging area in the chamber.

In a preferred embodiment, the loading area has an open elongated slot in the sidewall so that the forcep blades can easily be withdrawn after the lens is fully inserted in the staging area. The passageway preferably has a circular cross section at the proximal lens receiving end, which gradually tapers to join an elliptical passageway at the entrance to the staging area, where the IOL is completely deformed or compressed after it is pushed into the staging area.

The loading area may be somewhat flexible at the proximal end for making the deforming or compressing step easier, with the staging area being relatively rigid for maintaining the IOL in place in a deformed or compressed configuration as it is advanced. The compression chamber also includes a distal tip that is long enough to insert through a relatively small incision in the eye and is relatively flexible for enabling the IOL to be expressed into the patient's eye.

The compression chamber is designed to be mounted in a housing which has a slot for receiving a tab that projects from the outer surface of the compression chamber. The tab enables the chamber to be conveniently held when the IOL is deformed or compressed and to hold the chamber in the housing. The distal end of the loading chamber projects from the housing when the compression chamber is mounted in the housing. A plunger is associated with the inserter, which is movable through the passageway in the compression chamber, from the proximal end of the loading area, into engagement with the deformed or compressed lens in the staging area, to push the folded IOL through the distal tip and into the eye.

A compression chamber is therefore provided which has no moving parts so that an IOL can be inserted through a gradually-decreasing-diameter loading area with a pair of long-bladed forceps and pushed into a staging area. The walls of the loading area cause the IOL to be deformed and/or compressed. When the IOL is in the staging area it is in a position where it can easily be inserted into the eye after the compression chamber is mounted in a housing which has a single plunger for forcing the IOL out of the compression chamber.

BRIEF DESCRIPTION OF THE DRAWINGS

A better understanding of the invention can be obtained when the detailed description of exemplary embodiments set forth below is considered in conjunction with the appended drawings, in which:

FIG. 1 is a diagrammatic view of a foldable intraocular lens being inserted into an eye from a compression chamber made in accordance with the invention;

FIG. 2 is a perspective view of the compression chamber of FIG. 1, showing in particular a foldable IOL held by a pair of forceps ready to be inserted in the proximal end of the loading area of the compression chamber;

FIG. 3 is a perspective view of the compression chamber of FIG. 2, with the lens partially inserted in the loading area;

FIG. 4 is an end view looking along site line 4—4 of FIG. 3;

FIG. 5 is a perspective view of the compression chamber, partially broken away, with an IOL fully inserted in the staging area of the compression chamber;

FIG. 6 is an end view looking along the site line 6—6 of FIG. 5;

FIG. 7 is a sectional view of the compression chamber of FIGS. 2–6 mounted in an inserter as shown in FIG. 1, with a deformed and/or compressed IOL ready to be expressed into an eye;

FIG. 8 is a top plan view of the insertion of FIG. 7 looking along the site line 8—8 of FIG. 7;

FIG. 9 is a sectional view of the inserter shown in FIG. 7, with a plunger expressing the deformed or compressed IOL out of the distal end of the compression chamber;

FIG. 10 is a sectional view of the inserter of FIG. 9 looking along the site line 11—11 of FIG. 9;

FIG. 11 is a detailed sectional view of the proximal end of the inserter looking along the site line 12—12 of FIG. 9.

FIG. 12 is a fragmented plan view of a first alternative design of the distal tip of the compression chamber; and FIG. 13 is a fragmented plan view of a second alternative design of the distal tip.

DETAILED DESCRIPTION OF EXEMPLARY EMBODIMENTS

The subject invention is directed to a compression chamber 10, shown in detail in FIGS. 2–6, which is useful for rolling, folding or otherwise deforming or compressing an IOL 12 formed of a soft material such as, for example, silicon or a hydrogel, so the IOL can be inserted into the eye of a patient. As shown in FIG. 1, after the IOL 12 is deformed or compressed and positioned in a staging area in the compression chamber 10, as described in greater detail below, the compression chamber 10 is mounted in an insertion device, generally designated by reference numeral 14, for inserting the IOL 12 into a patient's eye 16 after an elongated distal tip 18 is inserted through an incision formed in the eye.

The compression chamber 10, shown in detail in FIGS. 2–6, includes a loading area 20 which is formed at a proximal end 22 of the compression chamber 10. The loading area 20 has an internal passageway that is generally circular in cross section and is sized to be about 0.160" in diameter at the proximal end 22, which is approximately the width of a leading edge 24 of the IOL 12 to allow for relatively easy insertion of the IOL 12 into the loading area 20. The opening may be elliptical, ovoid, circular, hexagonal or other appropriate shape.

As shown in FIG. 2, an IOL which has an optic portion 26 and a surrounding support or haptic portion 28, formed of a single piece of material, is shown ready to be inserted into the compression chamber 10. It should be understood, however, that IOLs formed of more than one piece of material such as, for example, an optic which has a pair of loops or haptics connected at the outer periphery of the optic (not shown) could also be used with the compression chamber 10.

The compression chamber 10 is preferably formed of a polypropylene polymer such as, for example, that sold by Huntsman Chemical Corp., No. 5B25Z. This material can easily be injection molded into the shape as shown and described, which will have a relatively smooth inner surface and can be sterilized.

Insertion of the IOL 12 into the compression chamber 10 is preferably done with a pair of forceps 30 which can either have angled forcep blades 32 as shown in FIGS. 2 and 3, or be of the straight-bladed variety (not shown). The blades 32 must be long enough so that they can grip the IOL 12 as shown and push it through the loading area 20 (see FIG. 3) and into a staging area 34 shown in FIG. 5.

Before the IOL 12 is inserted into the compression chamber 20, the loading area is lubricated by depositing an amount of a solution directly into the opening. This solution may be a known viscoelastic solution which is also typically injected into the eye during IOL surgery, which operates to protect cells and tissue on the inner surface of the cornea as well as maintain the shape of the eye during surgery. The solution may also be a balanced salt solution which is commonly used during eye surgery.

It has been found that for best results, solution should be generously applied to the interior of the compression chamber, but not to the outer surface of the IOL 12. This allows the forcep blades 32 to grip the IOL 12 firmly without slipping.

As shown best in the cross-sectional views in FIGS. 7 and 9, the loading area 20 is defined by a passageway which is cylindrical in cross section (or other appropriate shape) and gradually decreases in diameter from about 0.160" to about 0.101". The wall of the loading area 20 is thinner at the distal end 22 and gradually increases in width as the passageway approaches the staging area 34. The loading area 20 is formed with a slot 36 so that once the IOL is inserted in the staging area 34, the forcep blades 32 can easily be withdrawn. As shown in FIGS. 4 and 6, a groove 38 may be formed along the bottom surface of the wall that defines the loading area 20, opposite the slot 36, which facilitates withdrawal of the lower forcep blade 32.

Inclusion of the slot 36 and the relatively thin walls defining the loading area 20 provide flexibility to the walls so that as the IOL 12 is pushed from the position shown in FIG. 2 to the position shown in FIG. 3, and into the deformed or compressed position in a staging area 34 as shown in FIG. 5, the shaping of the IOL is more easily achieved. As shown in FIGS. 2 and 4, the IOL is inserted directly into the proximal end 22 of the loading area 20. As the IOL is pushed toward the staging area 34, the walls which define the loading area operate to cause the sides of the IOL 12 to curl upwardly. As the IOL is pushed toward the staging area 34, the diminishing-diameter surface of the loading area 20 causes the IOL to deform and compress from the position shown in FIG. 4 to the position shown in FIG. 6.

A pair of ridges 40 may be formed on the inner surface of the walls which define the loading area 20 for guiding the outer edges of the haptic portion 28 of the IOL 12. As shown in FIG. 4, when the IOL is initially inserted it is aligned beneath the ridges 40 As shown, in particular in FIG. 5, the ridges begin at approximately the center of the loading area 20 at the distal end 22, but move upwardly along the surface of the wall which defines the loading area 20 for guiding the edges of the haptics 28 into their curled position until they reach the staging area 34 shown in FIG. 6.

The staging area 34 is formed with a passageway that operates as a continuation of the passageway in the loading area 20. The staging area passageway also gradually diminishes in size along its length, but is preferably formed with an elliptical cross-section, instead of one which is circular. The passageway in the staging area 34 has a cross-sectional dimension adjacent to the loading area of 0.101" in the long dimension and 0.095" in the short dimension, which decreases in size in the short dimension until the passageway measures 0.101"/0.086". The wall of the compression chamber 10 which defines the staging area 34 is relatively thick so that as the IOL 12 is pushed into the staging area 34, the wall will not flex for maintaining the IOL in the deformed or compressed position shown in FIG. 6.

After the IOL 12 is loaded as described and shown, the compression chamber 10 is mounted in an insertion instrument 14 of a known type. This instrument may be formed of a sterilizable material such as stainless steel or titanium and includes a holding section 42 which has a slot 44 in which the compression chamber 10 is initially inserted. A tab or handle 48 is formed integral with the compression chamber 10 which, in addition to making the compression chamber 10 easy to hold during insertion of the IOL 12, fits snugly in a slot 46 for holding the compression chamber in place in the holding section 42. The distal tip 18 of the compression chamber 10 projects through an opening 50 formed on the distal end of the inserter 14 so that the distal tip 18 can be inserted through an incision formed in the outer surface of the eye 16 (see FIG. 1).

The distal tip 18 has a relatively thin wall and a passageway that is slightly elliptical in cross section, but which decreases in size along both the long and short dimensions of the ellipse. For example, the passageway in the distal tip 18 is 0.101"/0.086" adjacent to the staging area 34, and decreases to 0.097"/0.082" until it communicates with a truncated tip 52 which diminishes in size to its distal end to 0.085"/0.070" or smaller. As shown in the sectional views of FIGS. 7 and 9, the distal tip and truncated end have a relatively thin wall to allow some flexibility for enabling the IOL 12 to be expressed more easily as described in greater detail below. With the dimensions of the distal tip 13 and truncated end 52, an incision of about 2.8 mm or slightly more is needed in the eye 16.

The IOL 12 is moved from the staging area through the distal tip 18 and truncated end 52 by means of a plunger 54 movable within the inserter 14. The plunger 54 may have a threaded proximal end 56 which engages cooperating threads 58 formed internally in the inserter 14, so that when a knob 60 is rotated a plunger tip 62, formed in a known way into a cup-shape, is moved into engagement with the IOL 12. Further rotation of the knob 60 causes the plunger tip 62 to move forward to force the IOL 12 through the staging area 34 and distal tip 18 so that the IOL is expressed out of the truncated end 52 as shown in FIGS. 1 and 9.

As shown in particular in FIG. 10, a plug 64 is mounted in the inserter housing 14 to engage a flattened side 66 of the plunger 54 to prevent the plunger from rotating as it is moved forward. As shown in FIG. 11, the plunger 54 includes a flattened end 68, located in the knob 60, so that the knob 60 can rotate relative to the plunger 54 to move the plunger 54 forward for expressing the IOL as described. An end piece 70 is mounted in the knob 60 for bearing against the flattened head 68 and pushing the plunger 54 forward as the knob 60 is rotated.

The truncated tip 52 may be formed with a flat distal end 53 as shown in FIGS. 7–9 or, alternatively, other shapes which assist in expressing an IOL in various ways. For example, as shown in FIG. 12 the tip 53 may be beveled at an angle A of about 35°–50°, preferably about 45°, for allowing the IOL 12 to gradually unfold as it is expressed. The tip 52 may alternatively be formed with one or more slits 70 along the length of the truncated portion 52 for allowing the haptic portions to expand gradually prior to the optic being expressed from the distal end. For example, a single slit may be used so that the IOL can move toward the side of the slit as the IOL is expressed. A pair of the slits 70, for a single-piece IOL 12 or for multi-piece IOLs (not shown), are preferable so the IOL is expressed axially from the truncated tip 52. Obviously, other designs may be used for other types of expressing characteristics such as, for example, slots or other irregularly shaped openings.

Thus, a compression chamber for deforming and/or compressing an IOL has been described which is advantageous over all known compression chambers since an IOL is deformed or compressed exclusively through a single step of inserting an IOL into a staging area by means of a pair of forceps. There are no moving parts to complicate fabrication or to pinch the IOL during the folding process. The compression chamber is easily mounted in an insertion device so that the IOL can be pushed through the chamber and expressed into a proper location in the eye of a patient. This pushing is done through the use of a single plunger because the IOL has already been mounted in a staging area adjacent to the portion that is inserted into the eye. The compression chamber is designed to be flexible and rigid in respective strategic locations in order to enhance the ability of an operator to insert an IOL and deform or compress it with a pair of forceps in a single step, and then to express the IOL into a patient's eye.

It will become apparent to one of ordinary skill in the art that modifications and improvements can be made to the invention without departing from the spirit and scope of the invention, and it is contemplated that all such modifications and improvements will fall within the scope of the invention as defined in the appended claims.

What is claimed is:

1. An apparatus in which a deformable or compressible intraocular lens can be received and staged for insertion into a patient's eye, comprising:

(a) an elongated compression chamber having proximal and distal ends and a longitudinal passageway extending between the ends;

(b) the portion of the passageway adjacent to the proximal end forming a loading area in which the passageway gradually decreases in size for causing an intraocular lens to be deformed or compressed as the lens is moved along the passageway;

(c) a staging area communicating with the loading area where a portion of the passageway is sized to retain the intraocular lens in a deformed or compressed condition;

(d) the portion of the passageway defining the loading area comprising a wall which has at least a flexible portion at the proximal end of the chamber so the loading area can deform as an intraocular lens is pushed through the loading area and into the staging area;

(e) wherein the compression chamber is adapted to be inserted into a device for pushing a deformed or compressed intraocular lens inside the compression chamber through the passageway and out the distal end of the compression chamber.

2. The apparatus of claim 1, wherein the wall is relatively thin at least at the proximal end of the chamber adjacent the passageway defining the loading area.

3. The apparatus of claim 2, wherein the wall gradually increases in width from the proximal end of the chamber toward the portion of the passageway defining the staging area.

4. The apparatus of claim 1, wherein the loading chamber includes a slot formed in the wall extending from the proximal end of the chamber.

* * * * *